(12) United States Patent
Lochead et al.

(10) Patent No.: US 7,247,638 B2
(45) Date of Patent: Jul. 24, 2007

(54) 8-SUBSTITUTED-6,7,8,9-TETRAHYDRO-PYRIMIDO [1,2-A] PYRIMIDIN-4-ONE DERIVATIVES.

(75) Inventors: Alistair Lochead, Charenton (FR); Mourad Saady, Paris (FR); Franck Slowinski, Thieux (FR); Philippe Yaiche, Les Lilas (FR)

(73) Assignees: Sanofi-Aventis, Paris (FR); Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 11/225,218

(22) Filed: Sep. 13, 2005

(65) Prior Publication Data

US 2006/0035885 A1 Feb. 16, 2006

Related U.S. Application Data

(63) Continuation of application No. PCT/EP2004/004014, filed on Mar. 19, 2004.

(30) Foreign Application Priority Data

Mar. 21, 2003 (EP) .................................. 03290727

(51) Int. Cl.
C07D 487/04 (2006.01)
A61K 31/519 (2006.01)

(52) U.S. Cl. .................. 514/259.41; 544/279

(58) Field of Classification Search ............... 544/279; 514/259.41
See application file for complete search history.

(56) References Cited

FOREIGN PATENT DOCUMENTS

EP 1184383 3/2002
WO WO 02/18386 3/2002

OTHER PUBLICATIONS

Ulrich, Crystallization—4. Crystal Characteristics, Kirk-Othmer Encyclopedia of Chemical Technology, Aug. 2002.*

Vippagunta et al., Crystalline Solids, Advanced Drug Delivery Reviews, 48, pp. 3-26, 2001.*

West, Solid Solutions, Solid State Chemistry and its applications, pp. 358 & 365, 1988.*

Julien et al., PubMed Abstract (Prog Nucleic Acid Res Mol Biol. 61:1-23), 1998.*

Liu et al., PubMed Abstract (J Neurochem 87(6):1333-44), Dec. 2003.*

Damasio, Alzheimer's Disease and Related Dementias, Cecil Textbook of Medicine, 20th Edition, vol. 2, pp. 1992-1996, 1996.*

Layzer, Degenerative Diseases of the Nervous System, Cecil Textbook of Medicine, 20th Edition, vol. 2, pp. 2050-2057, 1996.*

Simone, Oncology: Introduction, Cecil Textbook of Medicine, 20th Edition, vol. 1, pp. 1004-1010, 1996.*

* cited by examiner

*Primary Examiner*—Deepak Rao
(74) *Attorney, Agent, or Firm*—Balaram Gupta

(57) ABSTRACT

The invention relates to substituted-pyrimidone derivatives represented by formula (I) or a salt thereof:

wherein X, Y, R1, R2, R3, R4, R5, n, p and q are as defined herein. The invention relates also to a medicament comprising the said derivative or a salt thereof as an active ingredient which is used for preventive and/or therapeutic treatment of a neurodegenerative disease caused by abnormal activity of GSK3β, such as Alzheimer's disease.

17 Claims, No Drawings

8-SUBSTITUTED-6,7,8,9-TETRAHYDRO-PYRIMIDO [1,2-A] PYRIMIDIN-4-ONE DERIVATIVES.

This application is a continuation of International application No. PCT/EP2004/004014, filed Mar. 19, 2004 which is incorporated herein by reference in its entirety; which claims the benefit of priority of European Patent Application No. 03290727.1, filed Mar. 21, 2003.

TECHNICAL FIELD

The present invention relates to compounds that are useful as an active ingredient of a medicament for preventive and/or therapeutic treatment of neurodegenerative diseases caused by abnormal activity of GSK3β.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several taupathies. Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β of β-catenin, a protein involved in cell survival, results in its degradation by an ubiquitinilation dependent proteasome pathway.

Thus, it appears that inhibition of GSK3β activity may result in neurotrophic activity. Indeed there is evidence that lithium, an uncompetitive inhibitor of GSK3β, enhances neuritogenesis in some models and also increases neuronal survival, through the induction of survival factors such as Bcl-2 and the inhibition of the expression of proapoptotic factors such as P53 and Bax.

Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Altogether these experimental observations indicate that GSK3β may find application in the treatment of the neuropathological consequences and the cognitive and attention deficits associated with Alzheimer's disease, as well as other acute and chronic neurodegenerative diseases. These include, in a non-limiting manner, Parkinson's disease, taupathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

In addition GSK3β, may find application in the treatment of other diseases such as: non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

DISCLOSURE OF THE INVENTION

An object of the present invention is to provide compounds useful as an active ingredient of a medicament for preventive and/or therapeutic treatment of a disease caused by abnormal GSK3β activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases. The present invention thus provides substituted-pyrimidone derivatives represented by formula (I) or salts thereof, solvates thereof or hydrates thereof:

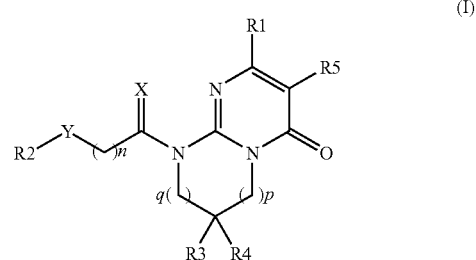

wherein:
X represents two hydrogen atoms, a sulfur atom, an oxygen atom or a $C_{1-2}$ alkyl group and a hydrogen atom;
Y represents a bond, a carbonyl group, a methylene group optionally substituted by one or two groups chosen from a $C_{1-6}$ alkyl group, a hydroxyl group, a $C_{1-4}$ alkoxy group, a $C_{1-2}$ perhalogenated alkyl group or an amino group;
R1 represents a 2, 3 or 4-pyridine ring or a 2, 4 or 5-pyrimidine ring, the rings being optionally substituted by a $C_{1-4}$ alkyl group, a $C_{1-4}$ alkoxy group, or a halogen atom;
R2 represents a phenyl group or a naphthalene ring; the phenyl group and the naphthalene ring being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a phenyl group, a pyrrolidine ring, a piperidine ring or an azepine ring;

R3 represents a hydrogen atom or a $C_{1-6}$ alkyl group;

R4 represents a phenyl group, a pyridinyl group or a naphthalene ring, the groups and the ring being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group or a $C_{2-10}$ dialkylamino group;

R5 represents a hydrogen atom, a $C_{1-6}$ alkyl group or a halogen atom; n represent 0 to 3; and p+q=0-3.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β activity, and the aforementioned medicament which is used for preventive and/or therapeutic treatment of neurodegenerative diseases and in addition other diseases such as: non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

As further preferred embodiments of the present invention, there are provided the aforementioned medicament wherein the diseases are neurodegenerative diseases and are selected from the group consisting of Alzheimer's disease, Parkinson's disease, taupathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma, and the aforementioned medicament in the form of pharmaceutical composition containing the above substance as an active ingredient together with one or more pharmaceutical additives.

The present invention further provides an inhibitor of GSK3β activity comprising as an active ingredient a substance selected from the group consisting of the substituted pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β activity, which comprises the step of administering to a patient a preventively and/or therapeutically effective amount of a substance selected from the group consisting of substituted pyrimidone derivatives of formula (I) and the physiologically acceptable salts thereof, and the solvates thereof and the hydrates thereof; and a use of a substance selected from the group consisting of the substituted pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The $C_{1-4}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl group represents an alkyl group wherein all of the hydrogens have been substituted by halogens, for example a $CF_3$ or $C_2F_5$;

The $C_{1-3}$ halogenated alkyl group represents an alkyl group wherein at least one hydrogen has not been substituted by a halogen atom;

The $C_{1-5}$ monoalkylamino group represents an amino group substituted by one $C_{1-6}$ alkyl group, for example, methylamino group, ethylamino group, propylamino group, isopropylamino group, butylamino group, isobutylamino group, tert-butylamino group, pentylamino group and isopentylamino group;

The $C_{2-10}$ dialkylamino group represents an amino group substituted by two $C_{1-5}$ alkyl groups, for example, dimethylamino group, ethylmethylamino group, diethylamino group, methylpropylamino group and diisopropylamino group;

A leaving group L represents a group which could be easily cleaved and substituted, such a group may be for example a tosyl, a mesyl, a bromide and the like.

P+q=0 to 3, indicates that the addition of p and q equals 0, 1, 2 or 3.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)-aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucoronic acid, ascorbic acid, nicotinic acid, and salicylic acid; or salts with acidic amino acids such as aspartic acid, and glutamic acid.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the substituted pyrimidone derivatives represented by the aforementioned formula (I) and salts thereof, their solvates and hydrates also fall within the scope of the present invention.

The substituted pyrimidone derivatives represented by the aforementioned formula (I) may have one or more asymmetric carbon atoms. As for the stereochemistry of such asymmetric carbon atoms, they may independently be in either (R) and (S) configuration, and the derivative may exist as stereoisomers such as optical isomers, or diastereoisomers. Any stereoisomers in pure form, any mixtures of stereoisomers, racemates and the like fall within the scope of the present invention.

Examples of compounds of the present invention are shown in table 1 hereinafter. However, the scope of the present invention is not limited by these compounds.

One of the embodiments of the present invention include also compounds represented by formula (I) wherein R1, R2, R3, R4, R5, X, Y, n, p and q are as defined hereunder:

(1) R1 represents a 3- or 4-pyridine ring and more preferably 4-pyridinyl ring or a 4- or 5-pyrimidine ring and more preferably 4-pyrimidinyl ring, which may be substituted by a $C_{1-2}$ alkyl group, a $C_{1-2}$ alkoxy group or a halogen atom;

(2) R2 represents a phenyl group or a naphthalene ring, the phenyl group and the naphthalene ring being optionally substituted 1 to 4 substituents selected from a $C_{1-3}$ alkyl group, a halogen atom, a hydroxyl group, a $C_{1-2}$ alkoxy group, a phenyl group, a pyrrolidine ring, a piperidine ring or an azepine ring;

(3) R3 represents a hydrogen atom;

(4) R4 represents a phenyl group, a pyridinyl group or a naphthalene ring;

(5) R5 represents a hydrogen atom;

(6) X represents two hydrogen atoms;

(7) Y represents a carbonyl group or methylene group being optionally substituted by one or two groups chosen from a $C_{1-3}$ alkyl group, a hydroxyl group, a $C_{1-4}$ alkoxy group, a $C_{1-2}$ perhalogenated alkyl group, an amino group;

(8) n, p and q represent 0, 2 and 0, respectively.

Another embodiment of the present invention include compounds represented by formula (I) wherein R1, R2, R3, R4, R5, X, Y, n, p and q are as defined hereunder:

(1) R1 represents an unsubstituted 4-pyridinyl ring or 4-pyrimidinyl ring;
alternatively R1 represents an unsubstituted 4-pyridinyl ring;

(2) R2 represents a phenyl group or a naphthalene ring, the phenyl group and the naphthalene ring being optionally substituted by 1 to 4 substituents selected from a $C_{1-3}$ alkyl group, a halogen atom, a hydroxyl group, a $C_{1-2}$ alkoxy group, a phenyl group, a pyrrolidine ring, a piperidine ring or an azepine ring;

(2) R3 represents a hydrogen atom;

(3) R4 represents a phenyl group or a pyridinyl group;

(4) R5 represents a hydrogen atom;

(5) X represents two hydrogen atoms;

(6) Y represents a carbonyl group or a methylene group optionally substituted by a hydroxyl group;

(7) n, p and q represent 0, 2 and 0, respectively.

Particularly compounds of the present invention represented by formula (I), wherein R4 is a 8-phenyl or a 8-pyridinyl group, include compounds of Table 1:

1. 1'-[(2S)-2-Hydroxy-2-phenyl-ethyl]-8-phenyl-2-(4-pyridinyl)-6,7,8,9-tetrahydro-4H-pyrimido[1,2-a]pyrimidin-4-one
2. 9-(2-Oxo-2-phenyl-ethyl)-8-phenyl-2-(4-pyridinyl)-6,7,8,9-tetrahydro-4H-pyrimido[1,2-a]pyrimidin-4-one
3. 9-[2-(3-Bromo-phenyl)-2-oxo-ethyl]-8-phenyl-2-(4-pyridinyl)-6,7,8,9-tetrahydro-4H-pyrimido[1,2-a]pyrimidin-4-one
4. 9-[2-(4-Chloro-phenyl)-2-oxo-ethyl]-8-phenyl-2-(4-pyridinyl)-6,7,8,9-tetrahydro-4H-pyrimido[1,2-a]pyrimidin-4-one
5. 9-[2-(4-Fluoro-phenyl)-2-oxo-ethyl]-8-phenyl-2-(4-pyridinyl)-6,7,8,9-tetrahydro-4H-pyrimido[1,2-a]pyrimidin-4-one
6. 9-[2-(3-Fluoro-phenyl)-2-oxo-ethyl]-8-phenyl-2-(4-pyridinyl)-6,7,8,9-tetrahydro-4H-pyrimido[1,2-a]pyrimidin-4-one
7. 9-[2-(4-Methoxy-phenyl)-2-oxo-ethyl]-8-phenyl-2-(4-pyridinyl)-6,7,8,9-tetrahydro-4H-pyrimido[1,2-a]pyrimidin-4-one
8. 9-[2-(Oxo-2-(4-pyrrolidin-1-yl-phenyl)-ethyl]-8-phenyl-2-(4-pyridinyl)-6,7,8,9-tetrahydro-4H-pyrimido[1,2-a]pyrimidin-4-one
9. 9-(2-Biphenyl-4-yl-2-oxo-ethyl)-8-phenyl-2-(4-pyridinyl)-6,7,8,9-tetrahydro-4H-pyrimido[1,2-a]pyrimidin-4-one
10. 9-(2-Oxo-2-p-tolyl-ethyl)-8-phenyl-2-(4-pyridinyl)-6,7,8,9-tetrahydro-4H-pyrimido[1,2-a]pyrimidin-4-one
11. 9-(2-Naphthalen-2-yl-2-oxo-ethyl)-8-phenyl-2-(4-pyridiny)-6,7,8,9-tetrahydro-4H-pyrimido[1,2-a]pyrimidin-4-one
12. 9-[2-(3-Methoxy-phenyl)-2-oxo-ethyl]-8-phenyl-2-(4-pyridinyl)-6,7,8,9-tetrahydro-4H-pyrimido[1,2-a]pyrimidin-4-one
13. 9-[2-(2-Methoxy-phenyl)-2-oxo-ethyl]-8-phenyl-2-(4-pyridinyl)-6,7,8,9-tetrahydro-4H-pyrimido[1,2-a]pyrimidin-4-one
14. 9-[(2S)-2-Oxo-2-phenyl-ethyl]-2,8-dipyridin-4-y-6,7,8,9-tetrahydro-4H-pyrimido[1,2-a]pyrimidin-4-one
15. 9-[2-(3-Bromo-phenyl)-2-oxo-ethyl]-2,8-dipyridin-4-yl-6,7,8,9-tetrahydro-pyrimido[1,2-a]pyrimidin-4-one
16. 9-(2-Hydroxy-2-phenyl-ethyl)-2,8-dipyridin-4-yl-6,7,8,9-tetrahydro-pyrimido[1,2-a]pyrimidin-4-one
17. 9-[2-(3-Bromo-phenyl)-2-hydroxy-ethyl]-2,8-dipyridin-4-yl-6,7,8,9-tetrahydro-pyrimido[1,2-a]pyrimidin-4-one
18. 9-[2-(3-Fluoro-phenyl)-2-oxo-ethyl]-2,8-dipyridin-4-yl-6,7,8,9-tetrahydro-pyrimido[1,2-a]pyrimidin-4-one
19. 9-[2-Hydroxy-2-(4-methoxy-phenyl)-ethyl]-8-phenyl-2-pyridin-4-yl-6,7,8,9-tetrahydro-pyrimido[1,2-a]pyrimidin-4-one
20. 9-(2-Hydroxy-2-p-tolyl-ethyl)-8-phenyl-2-pyridin-4-yl-6,7,8,9-tetrahydro-pyrimido[1,2-a]pyrimidin-4-one
21. (−)-9-(2-Oxo-2-phenyl-ethyl)-2,8-dipyridin-4-yl-6,7,8,9-tetrahydro-4H-pyrimido[1.2-a]pyrimidin-4-one
22. (+)-9-(2-Oxo-2-phenyl-ethyl)-2,8-dipyridin-4-yl-6,7,8,9-tetrahydro-4H-pyrimido[1.2-a]pyrimidin-4-one
23. 9-[2-Hydroxy-2-(3-bromo-phenyl)-ethyl]-8-phenyl-2-pyridin-4-yl-6,7,8,9-tetrahydro-pyrimido[1,2-a]pyrimidin-4-one
24. 9-[2-Hydroxy-2-(4-chloro-phenyl)-ethyl]-8-phenyl-2-pyridin-4-yl-6,7,8,9-tetrahydro-pyrimido[1,2-a]pyrimidin-4-one
25. 9-[2-(3-Fluoro-phenyl)-2-hydroxy-ethyl]-2,8-dipyridin-4-yl-6,7,8,9-tetrahydro-pyrimido[1,2-a]pyrimidin-4-one 26. 9-[2-Hydroxy-2-(4-fluoro-phenyl)-ethyl]-8-phenyl-2-pyridin-4-yl-6,7,8,9-tetrahydro-pyrimido[1,2-a]pyrimidin-4-one
27. 9-[2-Hydroxy-2-(4-phenyl-phenyl)-ethyl]-8-phenyl-2-pyridin-4-yl-6,7,8,9-tetrahydro-pyrimido[1,2-a]pyrimidin-4-one; and
28. 9-[2-Hydroxy-2-naphthalen-2-yl-ethyl]-8-phenyl-2-pyridin-4-yl-6,7,8,9-tetrahydro-pyrimido[1,2-a]pyrimidin-4-one As a further object, the present invention concerns also methods for preparing the substituted pyrimidone compounds represented by the aforementioned formula (I). These compounds can be prepared, for example, according to methods explained below.

Preparation Method

Substituted pyrimidone compounds represented by the aforementioned formula (I), may be prepared according to the method described in the scheme 1.

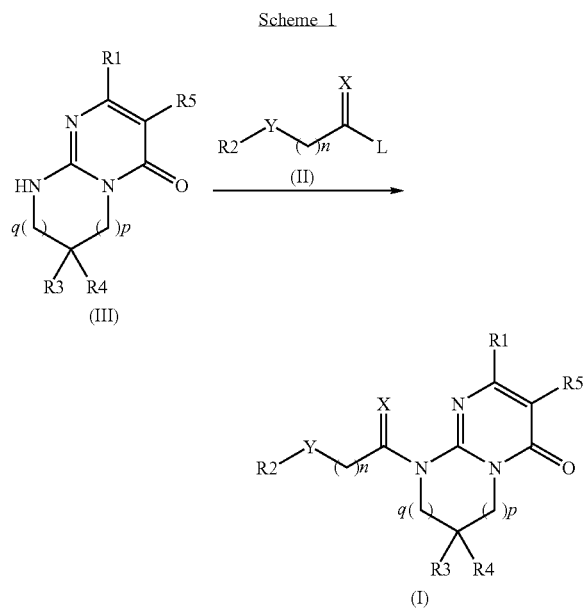

Following this method, the pyrimidinone derivative represented by the above formula (III), wherein R1, R3, R4, R5, p and q are as defined for compound of formula (I), is allowed to react with a base such as sodium hydride, sodium carbonate or potassium carbonate in a solvent such as N,N-dimethylformamide, N-methylpyrrolidone, N,N-dimethylacetamide or chloroform at a suitable temperature ranging from 0 to 130° C. under ordinary air, then with a compound of formula (II), wherein R2, X, Y and n are as defined for compound of formula (I) and L represents a leaving group preferably bromide or mesyl group, to obtain the compound of the aforementioned formula (I).

Alternatively compounds of formula (I) wherein Y represents a carbonyl group may be prepared by oxidation of a compound of formula (I) wherein Y represents a methylene group substituted by a hydroxyl group according to well known methods to one skilled in the art.

Compound of formula (II) is commercially available or may be synthesized according to well-known methods to one skilled in the art.

Compound of formula (III) may be prepared according to the method defined in scheme 2.

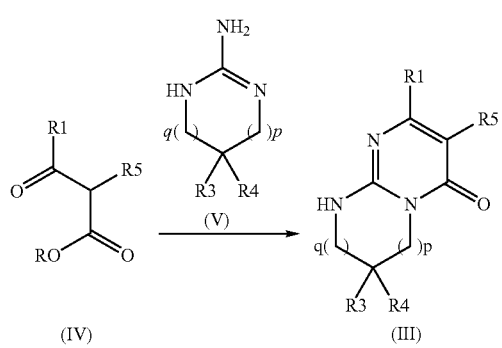

In the above scheme, L represents a leaving group, preferably a bromide or a mesyl group.

According to this method, the 3-ketoester of formula (IV), wherein R1 and R5 are as defined for compound of formula (I) and R is an alkyl group such as for example methyl or ethyl, is allowed to react with a compound of formula (V), wherein R3, R4, p and q are the same as those already described for compound of formula (I). The reaction may be carried out in the presence of a base such as potassium carbonate, in an alcoholic solvent such as methanol, ethanol and the like or without, at a suitable temperature ranging from 25° to 140° C. under ordinary air.

Alternatively, compound of formula (III) wherein R5 represents a hydrogen atom may be halogenated in order to give compounds of formula (III) wherein R5 is a halogen atom such as a bromine atom or a chlorine atom. The reaction may be carried out in an acidic medium such as acetic acid or propionic acid, in presence of bromosuccinimide or chlorosuccinimide, or bromine.

In addition, compounds of formula (III) wherein R5 represents a fluorine atom may be obtained by analogy to the method described in Tetrahedron Letters, Vol. 30, No. 45, pp 6113-6116, 1989.

Compound of formula (IV) is commercially available or may be synthesized according to well-known methods to one skilled in the art.

For example compounds of formula (IV), wherein R1 represent a pyridine ring or a pyrimidine ring, optionally substituted by a $C_{1-4}$ alkyl group, $C_{1-4}$ alkoxy group or a halogen atom, can be prepared by reacting respectively an isonicotinic acid or a pyrimidine-carboxylic acid, optionally substituted by a $C_{1-4}$ alkyl group, $C_{1-4}$ alkoxy group or a halogen, with the corresponding malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

In the above reactions, protection or deprotection of a functional group may sometimes be necessary. A suitable protecting group Pg can be chosen depending on the type of the functional group, and a method described in the literature may be applied. Examples of protecting groups, of protection and deprotection methods are given for example in Protective groups in Organic Synthesis Greene et al., 2nd Ed. (John Wiley & Sons, Inc., New York).

Compound of formula (V) is commercially available or may be synthesized according to well-known methods to one skilled in the art.

Alternatively, compound of formula (V), wherein p represents 2 and q represents 0, may be prepared according to the method defined in scheme 3. In the scheme 3 below, Pg represents an amino-protecting group and L a leaving group, preferably a bromide group or mesyl group.

Scheme 3

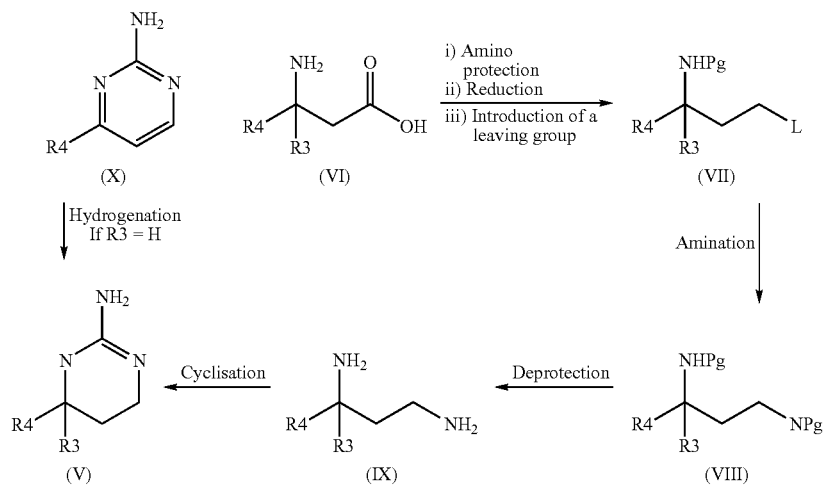

According to this method, compound of formula (VI), wherein R4 is defined as for compound of formula (I), may be obtained through different manners, depending on R3.

The 3-aminoacid of formula (VI), wherein R3 is a hydrogen atom, may be synthesized by analogy to the method described in Tetrahedron Letters, Vol. 43, No. 11, pp 1977-1981, 2002.

The 3-aminoacid of formula (VI), wherein R3 is a $C_{1-6}$ alkyl group, may be synthesized by analogy to the method described in Journal of Organic Chemistry, Vol. 56, No. 1, pp 4-6, 1991.

In both cases, an amino-protecting group is necessary. Examples of protection and deprotection methods are given for example in Protective groups in Organic Synthesis Greene et al., 2nd Ed. (John Wiley & Sons, Inc., New York).

By analogy to these methods, compounds of formula (VII) and (VIII) may be obtained by amino protection and compound of formula (IX) may be obtained by deprotection.

Then, compound of formula (V) may be obtained by cyclization, according to well-known methods to one skilled in the art.

Alternatively, if R3 represents H, compound of formula (V) may be obtained by hydrogenation of compound of formula (X), according to well-known methods to one skilled in the art.

Compound of formula (X) is commercially available or may be synthesized according to well-known methods to one skilled in the art.

As a further object, the present invention concerns also the compound of formula (III) as intermediate for preparing compounds of formula (I).

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, taupathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

The present invention will be explained more specifically with reference to the following general examples, however, the scope of the present invention is not limited to these examples.

Example 1 (Compound No. 2 of Table 1)

9-(2-Oxo-2-phenyl-ethyl)-8-phenyl-2-(4-pyridinyl)-6,7,8,9-tetrahydro-4H-pyrimido[1.2-a]pyrimidin-4-one hydrochloride (1:1)

1.1 6-Phenyl-1,4,5,6-tetrahydro-2-pyrimidinamine hydrochloride (1:2)

To a solution of 5 g (29.2 mmoles) of 2-amino-4-phenylpyrimidine in 30 ml of a 6N solution of hydrochloric acid in isopropanol was added 0.1 g of palladium on carbon catalyst (10% wt/wt). The suspension was hydrogenated under 40 psi pressure at room temperature during 3 h. The catalyst was removed by filtration and the solvent evaporated under reduced pressure. Diethyl ether was added and the resulting solution was refiltered and the solvent removed by evaporation under reduced pressure to give 4.0 g (55%) of compound as a crude oil which was used as such.

1.2 8-Phenyl-2-(4-pyridinyl)-6,7,8,9-tetrahydro-4H-pyrimido[1.2-a]pyrimidin-4-one A suspension containing 4 g (16.12 mmoles) of 6-phenyl-1,4,5,6-tetrahydro-2-pyrimidinamine hydrochloride (1:2), 3.11 g (16.12 mmoles) of ethyl 3-(pyridin-4-yl)-3-oxopropionate, 6.68 g (48.36 mmoles) of anhydrous potassium carbonate in 50 ml of ethanol were refluxed for 18 h. The cooled solution was evaporated and the residue was treated with water and allowed to stir at 0° C. during 2 h. The precipitate which formed was recovered by filtration and dried at 90° C. during 18 h. 4.80 g (98%) of product was thus obtained.

1.3 9-(2-Oxo-2-phenyl-ethyl)-8-phenyl-2-(4-pyridinyl)-6,7,8,9-tetrahydro-4H-pyrimido[1,2-a]pyrimidin-4-one hydrochloride (1:1)

A solution of 0.3 g (98 mmoles) of 8-phenyl-2-(4-pyridinyl)-6,7,8,9-tetrahydro-4H-pyrimido[1.2-a]pyrimidin-4-one in 8 ml of anhydrous dimethylformamide was treated with 51 mg (1.28 mmoles) of sodium hydride (60% in mineral oil). The resulting suspension was stirred at 0° C. for 30 mins and then treated with 0.255 g (1.28 mmoles) of 2-bromoacetophenone. After stirring for 18 h at room temperature, water was added and the reaction mixture was extracted with ethyl acetate. The organic phase was washed with a saturated solution of aqueous sodium chloride and was evaporated under reduced pressure to give crude product. Purification using silica gel chromatography eluting with a gradient comprising dichloromethane/methanol in the proportions 99/1 to 95/5 gave pure product which was dissolved in ethanol and treated with 1 equivalent of a solution of hydrochloric acid in isopropanol. The resulting salt was recrystallized from a mixture of isopropanol/diisopropylether to give 0.16 g (39%) of pure product. Mp: 134-137° C.

¹H NMR (200 MHz; DMSO-d⁶): δ (ppm) 8.6 (d, 2H); 8.0 (d, 2H); 7.6 (d, 1H); 7.5 (t, 2H); 7.3 (m, 5H); 6.6 (s, 1H); 5.7 (d, 1H); 5.1 (br s, 1H); 4.5 (m, 2H); 3.2 (ddd, 1H); 2.2 (m, 2H).

Example 2 (Compound No. 1 of Table 1)

1'-[(2S)-2-Hydroxy-2-phenyl-ethyl]-8-phenyl-2-(4-pyridinyl)-6,7,8,9-tetrahydro-4H-pyrimido[1,2-a]pyrimidin-4-one hydrochloride (1:1)

The product was obtained by analogy with the method described in Example 1.3, but replacing 2-bromoacetophenone by (1S)-2-chloro-1-phenyl ethanol. Mp: 254-256° C.
¹H NMR (200 MHz; DMSO-d⁶): δ (ppm) 8.9 (m, 2H); 8.3 (m, 2H); 7.5-7.1 (m, 10H); 6.6 (m, 1H); 5.3-5.0 (m, 2H); 4.6-4.0 (m, 3H); 3.2-2.7 (m, 2H); 2.5-1.8 (m, 2H).

Example 3 (Compound No. 3 of Table 1)

9-[2-(3-Bromo-phenyl)-2-oxo-ethyl]-8-phenyl-2-(4-pyridinyl)-6,7,8,9-tetrahydro-4H-pyrimido[1,2-a]pyrimidin-4-one hydrochloride (1:1)

The product was obtained by analogy with the method described in Example 1.3, but replacing 2-bromoacetophenone by 3-bromo-(2-bromoacetophenone). Mp: 143-145° C.
¹H NMR (200 MHz; DMSO-d⁶): δ (ppm) 8.7 (d, 2H); 8.2-7.8 (m, 5H); 7.5-7.2 (m, 7H); 6.6 (s, 1H); 5.7 (d, 1H); 5.1 (br s, 1H); 4.5 (d, 1H); 4.3 (m, 1H); 3.2 (ddd, 1H); 2.4-2.1 (m, 2H).

Example 4 (Compound No. 4 of Table 1)

9-[2-(4-Chloro-phenyl)-2-oxoethyl]-8-phenyl-2-(4-pyridinyl)-6,7,8,9-tetrahydro-4H-pyrimido[1,2-a]pyrimidin-4-one hydrochloride (1:1)

The product was obtained by analogy with the method described in Example 1.3, but replacing 2-bromoacetophenone by 4-chloro-(2-bromoacetophenone). Mp: 145-147° C.
¹H NMR (200 MHz; DMSO-d⁶): δ (ppm) 8.7 (d, 2H); 8.1 (m, 4H); 7.6 (d, 2H); 7.4 (m, 5H); 6.7 (s, 1H); 5.7 (d, 1H); 5.1 (br s, 1H); 4.5 (d, 1H); 4.3 (m, 1H); 3.2 (ddd, 1H); 2.4-2.1 (m, 2H).

Example 5 (Compound No. 5 of Table 1)

9-[2-(4-Fluoro-phenyl)-2-oxo-ethyl]-8-phenyl-2-(4-pyridinyl)-6,7,8,9-tetrahydro-4H-pyrimido[1,2-a]pyrimidin-4-one hydrochloride (1:1)

The product was obtained by analogy with the method described in Example 1.3, but replacing 2-bromoacetophenone by 4-fluoro-(2-bromoacetophenone). Mp: 145-147° C.
¹H NMR (200 MHz; DMSO-d⁶): δ (ppm) 8.7 (d, 2H); 8.1 (m, 4H); 7.6 (m, 8H); 6.6 (s, 1H); 5.7 (d, 1H); 5.1 (br s, 1H); 4.5 (m, 1H); 4.3 (br s, 1H); 3.2 (ddd, 1H); 2.4-2.1 (m, 2H).

Example 6 (Compound No. 6 of Table 1)

9-[2-(3-Fluoro-phenyl)-2-oxo-ethyl]-8-phenyl-2-(4-pyridinyl)-6,7,8,9-tetrahydro-4H-pyrimido[1,2-a]pyrimidin-4-one hydrochloride (1:1)

The product was obtained by analogy with the method described in Example 1.3, but replacing 2-bromoacetophenone by 3-fluoro-(2-bromoacetophenone). Mp: 167-169° C.
¹H NMR (200 MHz; DMSO-d⁶): δ (ppm) 8.7 (d, 2H); 8.1 (d, 2H); 7.8 (m, 2H); 7.6-7.2 (m, 7H); 6.6 (s, 1H); 5.7 (d, 1H); 5.1 (br s, 1H); 4.5 (d, 1H); 4.4 (m, 1H); 3.2 (ddd, 1H); 2.4-2.1 (m, 2H).

Example 7 (Compound No. 7 of Table 1)

9-[2-(4-Methoxy-phenyl)-2-oxo-ethyl]-8-phenyl-2-(4-pyridinyl)-6,7,8,9-tetrahydro-4H-pyrimido[1,2-a]pyrimidin-4-one hydrochloride (1:1)

The product was obtained by analogy with the method described in Example 1.3, but replacing 2-bromoacetophenone by 4-methoxy-(2-bromoacetophenone). Mp: 197-199° C.
¹H NMR (200 MHz; CDCl₃): δ (ppm) 8.5 (d, 2H); 8.0 (d, 2H); 7.6-7.2 (m, 7H); 7.0 (d, 2H); 6.5 (s, 1H); 5.8 (d, 1H); 5.0 (dd, 1H); 4.5 (m, 1H); 4.1 (d, 1H); 3.9 (s, 3H); 3.5 (ddd, 1H); 2.6 (m, 1H); 2.3 (m, 1H).

Example 8 (Compound No. 8 of Table 1)

9-[2-(Oxo-2-(4-pyrrolidin-1-yl-phenyl)-ethyl]-8-phenyl-2-(4-pyridinyl)-6,7,8,9-tetrahydro-4H-pyrimido[1,2-a]pyrimidin-4-one The product was obtained by analogy with the method described in Example 1.3, but replacing 2-bromoacetophenone by 4-N-pyrrolidinyl-(2-bromoacetophenone). Mp: 253-255° C.
¹H NMR (200 MHz; CDCl₃): δ (ppm) 8.5 (d, 2H); 7.9 (d, 2H); 7.6 (d, 2H); 7.5-7.3 (m, 7H); 6.6 (d, 2H); 6.4 (s, 1H); 5.9 (d, 1H); 5.0 (br s, 1H); 4.5 (m, 1H); 4.1 (d, 1H); 3.6-3.3 (m, 5H); 2.6 (m, 1H); 2.3-2.0 (m, 5H).

Example 9 (Compound No. 9 of Table 1)

9-(2-Biphenyl-4-yl-2-oxo-ethyl)-8-phenyl-2-(4-pyridinyl)-6,7,8,9-tetrahydro-4 H-pyrimido[1,2-a]pyrimidin-4-one The product was obtained by analogy with the method described in Example 1.3, but replacing 2-bromoacetophenone by 4-phenyl-(2-bromoacetophenone). Mp: 222-224° C.
¹H NMR (200 MHz; CDCl₃): δ (ppm) 8.5 (d, 2H); 8.2 (d, 2H); 7.8-7.6 (m, 4H); 7.5-7.3 (m, 8H); 7.2 (d, 2H); 6.5 (s, 1H); 5.9 (d, 1H); 5.0 (br s, 1H); 4.5 (m, 1H); 4.2 (d, 1H); 3.6 (ddd, 1H); 2.7 (m, 1H); 2.3 (m, 1H).

Example 10 (Compound No. 10 of Table 1)

9-(2-Oxo-2-p-tolyl-ethyl)-8-phenyl-2-(4-pyridinyl)-6,7,8,9-tetrahydro-4H-pyrimido[1,2-a]pyrimidin-4-one The product was obtained by analogy with the method described in Example 1.3, but replacing 2-bromoacetophenone by 4-methyl-(2-bromoacetophenone). Mp: 209-211° C.
¹H NMR (200 MHz; CDCl₃): δ (ppm) 8.5 (d, 2H); 7.9 (d, 2H); 7.6-7.2 (m, 9H); 6.5 (s, 1H); 5.8 (d, 1H); 4.9 (br s, 1H); 4.5 (m, 1H); 4.1 (d, 1H); 3.6 (ddd, 1H); 2.6 (m, 1H); 2.5 (s, 3H); 2.2(m, 1H).

Example 11 (Compound No. 11 of Table 1)

9-(2-Naphthalen-2-yl-2-oxo-ethyl)-8-phenyl-2-(4-pyridinyl)-6,7,8,9-tetrahydro-4H-pyrimido[1,2-a]pyrimidin-4-one The product was obtained by analogy with the method described in Example 1.3, but replacing 2-bromoacetophenone by 2-bromoacetylnaphthalene. Mp: 226-228° C.

$^1$H NMR (200 MHz; CDCl$_3$): δ (ppm) 8.6 (s, 1 H); 8.4 (d, 2H); 8.1-7.9 (m, 4H); 7.7-7.5 (m, 2H); 7.4-7.2 (m, 7H); 6.45 (s, 1H); 6.0 (d, 1H); 5.0 (br s, 1H); 4.6 (m, 1H); 4.3 (d, 1H); 3.6 (ddd, 1H); 2.7 (m, 1H); 2.3 (m, 1H).

Example 12 (Compound No. 12 of Table 1)

9-[2-(3-Methoxy-phenyl)-2-oxo-ethyl]-8-phenyl-2-(4-pyridinyl)-6,7,8,9-tetrahydro-4H-pyrimido[1,2-a]pyrimidin-4-one The product was obtained by analogy with the method described in Example 1.3, but replacing 2-bromoacetophenone by 3-methoxy-(2-bromoacetophenone). Mp: 216-218° C.

$^1$H NMR (200 MHz; CDCl$_3$): δ (ppm) 8.5 (d, 2H); 7.7-7.2 (m, 11H); 6.45 (s, 1H); 5.85 (d, 1H); 4.9 (brs, 1H); 4.65 (m, 1H); 4.15 (d, 1H); 3.85 (s, 3H); 2.55 (ddd, 1H); 2.65 (m, 1H); 2.3 (m, 1H).

Example 13 (Compound No. 13 of Table 1)

9-[2-(2-Methoxy-phenyl)-2-oxo-ethyl]-8-phenyl-2-(4-pyridinyl)-6,7,8,9-tetrahydro-4H-pyrimido[1,2-a]pyrimidin-4-one The product was obtained by analogy with the method described in Example 1.3, but replacing 2-bromoacetophenone by 2-methoxy-(2-bromoacetophenone). Mp: 142-144° C.

$^1$H NMR (200 MHz; DMSO-d$^6$): δ (ppm) 8.7 (d, 2H); 8.0 (d, 2H); 7.6 (m, 2H); 7.4 (m, 5H); 7.2 (d, 1H); 7.1 (t, 1H); 6.6 (s, 1H); 5.5 (d, 1H); 5.0 (br s, 1H); 4.3 (d, 2H); 3.8 (s, 3H); 3.5 (m, 1H); 3.3 (ddd, 1H); 2.4-2.1 (m, 2H).

Example 14 (Compound No. 14 of Table 1)

9-[(2S)-2-Oxo-2-phenyl-ethyl]-2,8-dipyridin-4-yl-6,7,8,9-tetrahydro-4H-pyrimido[1,2-a]pyrimidin-4-one hydrochloride (1:2)

14.1 6-(4-Pyridinyl)-1,4,5,6-tetrahydro-2-pyrimidinamine hydrochloride (1:2)

To a solution of 5 g (29.2 mmoles) of 2-amino-4-(4-pyrimidyl)-pyrimidine (Journal of Medicinal Chemistry (1978), 21(7), 623-8) in 30 ml of a 6N solution of hydrochloric acid in isopropanol was added 5 ml of water and 0.2 g of palladium on carbon catalyst (10% wt/wt). The suspension was hydrogenated under 40 psi pressure at 50° C. temperature during 8 h. The catalyst was removed by filtration and the solvent evaporated under reduced pressure. Isopropanol was added and the resulting solution was refiltered and the solvent removed by evaporation under reduced pressure to give 2.0 g (27%) of compound as a white powder which was used as such.

14.2 2,8-Dipyridin-4-yl-6,7,8,9-tetrahydro-4H-pyrimido[1,2-a]pyrimidin-4-one A suspension containing 1.0 g (4.01 mmoles) of 6-(4-pyridinyl)-1,4,5,6-tetrahydro-2-pyrimidinamine dihydrochloride in 30 ml of ethanol was treated with 1.94 g (14.05 mmoles) of potassium carbonate and allowed to stir for 5 min. 1.0 g (4.01 mmoles) of ethyl 3-(pyridin-4-yl)-3-oxopropionate were added and the resulting mixture was heated at reflux temperature for 18 h. The cooled solution was evaporated to remove solvent and the residue was dissolved in water and extracted with dichloromethane. The organic extracts were washed with a saturated solution of aqueous sodium chloride, dried and the solvent evaporated under reduced pressure. The crude product thus obtained was purified using silica gel chromatography eluting with a gradient of dichloromethane/methanol/concentrated aqueous ammonia solution in the proportions 95/5/0.5 to 80/20/2. 0.26 g (21%) of pure product was obtained. Mp: 268-270° C.

14.3 9-[(2S)-2-Oxo-2-phenyl-ethyl]-2,8-dipyridin-4-yl-6,7,8,9-tetrahydro-4H-pyrimido[1,2-a]pyrimidin-4-one hydrochloride (1:2)

A suspension of 0.30 g (0.98 mmole) of 2,8-di-4-pyridinyl-6,7,8,9-tetrahydro-4H-pyrimido[1,2-a]pyrimidin-4-one in 6 ml of dimethylformamide was treated with 51 mg (1.28 mmole) of sodium hydride (60% in mineral oil) and the resulting suspension stirred at 35° C. for 30 mins. The mixture was then cooled to 0° C. and was treated with 0.235 g (1.18 mmole) of 2-bromoacetophenone and stirred for 4 h at room temperature. Water was added and the mixture extracted with dichloromethane. The organic extracts were washed with a saturated aqueous solution of sodium chloride and dried and evaporated. The crude product thus obtained was purified using silica gel chromatography eluting with a gradient of dichloromethane/methanol in the proportions 99/1 to 90/10. The pure product obtained was then dissolved in ethanol and treated with 1 equivalent of a solution of hydrochloric acid in isopropanol to give the hydrochloride salt. The resulting salt was recrystallized from a mixture of isopropanol/diisopropylether to give 0.20 g (48%) of pure product. Mp: 246-248° C.

$^1$H NMR (200 MHz; DMSO-d$^6$): δ (ppm) 8.9 (d, 2H); 8.7 (d, 2H); 8.0 (m, 6H); 7.8-7.5 (m, 3H); 6.7 (s, 1H); 5.75 (d, 1H); 5.3 (br s, 1H); 4.7 (d, 1H); 4.5 (m, 1H); 3.1 (ddd, 1H); 2.5 (m, 2H).

Example 15 (Compound No. 15 of Table 1)

9-[2-(3-Bromo-phenyl)-2-oxo-ethyl]-2,8-dipyridin-4-yl-6,7,8,9-tetrahydro-pyrimido[1,2-a]pyrimidin-4-one hydrochloride (1:2)

The product was obtained by analogy with the method described in Example 2.3, but replacing 2-bromoacetophenone by 3-bromo-(2-bromoacetophenone). Mp: 215-217° C.

$^1$H NMR (200 MHz; DMSO-d$^6$): δ (ppm) 8.9 (d, 2H); 8.7 (d, 2H); 8.3-7.8 (m, 7H); 7.5 (t, 1H); 6.7 (s, 1H); 5.75 (d, 1H); 5.3 (br s, 1H); 4.7 (d, 1H); 4.5 (m, 1H); 3.1 (ddd, 1H); 2.5 (m, 2H).

Example 16 (Compound No. 16 of Table 1)

9-(2-Hydroxy-2-phenyl-ethyl)-2,8-dipyridin-4-yl-6,7,8,9-tetrahydro-pyrimido[1,2-a]pyrimidin-4-one hydrochloride (1:2)

The product was obtained by analogy with the method described in Example 2.3, but replacing 2-bromoacetophenone by (1-S)-2-chloro-1-phenyl ethanol.
Mp: 204-206° C.
$^1$H NMR (200 MHz; DMSO-d$^6$): δ (ppm) 9.0 (m, 2H); 8.8 (m, 2H); 8.45 (m, 2H); 7.9 (d, 1H); 7.8-7.6 (m, 1H); 7.5-7.2 (m, 5H); 6.8 (s, 1H); 6.2-5.7 (br d, 1H); 5.3-5.1 (m, 1H); 4.6-4.1 (m, 2H); 3.3 (m, 2H); 2.9 (m, 1H); 2.5-2.2 (m, 2H).

Example 17 (Compound No. 17 of Table 1)

9-[2-(3-Bromo-phenyl)-2-hydroxy-ethyl]-2,8-dipyridin-4-yl-6,7,8,9-tetrahydro-pyrimido[1,2-a]pyrimidin-4-one The product was obtained by analogy with the method described in Example 2.3, but replacing 2-bromoacetophenone by 2-chloro-1-(3-bromo-phenyl)-ethanol. Mp: 190-192° C.
$^1$H NMR (200 MHz; CDCl$_3$): δ (ppm) 8.8 (d, 2H); 8.7 (d, 2H); 7.8 (m, 2H); 7.7-7.4 (m, 2H); 7.3 (m, 2H); 7.1 (d, 2H); 6.5 (s, 1H); 5.2 (m, 2H); 4.8-4.4 (m, 3H); 3.2 (m, 2H); 2.3 (m, 2H).

Example 18 (Compound No. 18 of Table 1)

9-[2-(3-Fluoro-phenyl)-2-oxo-ethyl]-2,8-dipyridin-4-yl-6,7,8,9-tetrahydro-pyrimido[1,2-a]pyrimidin-4-one one hydrochloride (1:2)

The product was obtained by analogy with the method described in Example 2.3, but replacing 2-bromoacetophenone by 3-fluoro-(2-bromoacetophenone). Mp: 132-134° C.
$^1$H NMR (200 MHz; DMSO-d$^6$): δ (ppm) 8.9 (d, 2H); 8.7 (d, 2H); 8.1 (d, 2H); 8.0 (d, 2H); 7.9-7.7 (m, 2H); 7.7-7.5 (m, 2H); 6.8 (s, 1H); 5.7 (d, 2H); 5.3 (br s, 1H); 4.7 (d, 1H); 4.4 (m, 1H); 3.1 (ddd, 1H); 2.4 (m, 1H).

Example 19 (Compound No. 19 of Table 1)

9-[2-Hydroxy-2-(4-methoxy-phenyl)-ethyl]-8-phenyl-2-pyridin-4-yl-6,7,8,9-tetrahydro-pyrimido[1,2-a]pyrimidin-4-one The product was obtained by analogy with the method described in Example 1.3, but replacing 2-bromoacetophenone by 2-chloro-1-(4-methoxy-phenyl) ethanol. Mp: 150-152° C.
$^1$H NMR (200 MHz; CDCl$_3$): δ (ppm) 8.8 (d, 2H); 7.9 (d, 2H); 7.6-7.2 (m, 6H); 7.1 (m, 2H); 6.9 (m, 2H); 5.3-5.0 (m, 2H); 4.8-4.4 (m, 3H); 3.8 (m, 3H); 3.4-3.0 (m, 2H); 2.4-2.0 (m, 2H).

Example 20 (Compound No. 20 of Table 1)

9-(2-Hydroxy-2-p-tolyl-ethyl)-8-phenyl-2-pyridin-4-yl-6,7,8,9-tetrahydro-pyrimido[1,2-a]pyrimidin-4-one The product was obtained by analogy with the method described in Example 1.3, but replacing 2-bromoacetophenone by 2-chloro-1-(4-methylphenyl)-ethanol. Mp: 198-200° C.

$^1$H NMR (200 MHz; CDCl$_3$): δ (ppm) 8.8 (d, 2H); 7.8 (d, 2H); 7.4-7.0 (m, 8H); 6.5 (s, 1H); 5.2 (m, 1H); 4.8-4.4 (m, 5H); 3.4-3.0 (m , 2H); 2.5-2.0 (m, 5H).

Example 21 (Compound No. 21 of Table 1)

(−)-9-(2-Oxo-2-phenyl-ethyl)-2,8-dipyridin-4-yl-6,7,8,9-tetrahydro-4H-pyrimido[1,2-a]pyrimidin-4-one hydrochloride (1:2)

21.1 (+)-2,8-Dipyridin-4-yl-6,7,8,9-tetrahydro-4H-pyrimido[1,2-a]pyrimidin-4-one 1.2 g (3.93 mmol) of 2,8-dipyridin-4-yl-6,7,8,9-tetrahydro-4H-pyrimido[1,2-a]pyrimidin-4-one (compound No. 14.2) was separated by chiral preparative HPLC (CHIRALPAK AS) eluting with n-heptane/ethanol in the proportions 50/50 to give 0.572 g of pure product obtained in the form of free base. $t_R$: 7 min. Mp: 235-238° C. $[\alpha]_D^{20}$=+11.3° (c=0.44, DMSO).

21.2 (−)-9-(2-Oxo-2-phenyl-ethyl)-2,8-dipyridin-4-yl-6,7,8,9-tetrahydro-4H-pyrimido[1,2-a]pyrimidin-4-one hydrochloride (1:2)

The product was obtained by analogy with the method described in Example 14.3. Mp: 225-227° C. $[\alpha]_D^{20}$=−63.1° (c=0.356, DMSO).
$^1$H NMR (200 MHz; DMSO-d$^6$): δ (ppm) 8.9 (d, 2H); 8.7 (d, 2H); 8.0 (m, 6H); 7.8-7.5 (m, 3H); 6.7 (s, 1H); 5.75 (d, 1H); 5.3 (br s, 1H); 4.7 (d, 1H); 4.5 (m, 1H); 3.1 (ddd, 1H); 2.5 (m, 2H).

Example 22 (Compound No. 22 of Table 1)

(+)-9-(2-Oxo-2-phenyl-ethyl)-2,8-dipyridin-4-yl-6,7,8,9-tetrahydro-4H-pyrimido[1,2-a]pyrimidin-4-one hydrochloride (1:2)

22.1 (−)-2,8-Dipyridin-4-yl-6,7,8,9-tetrahydro-4H-pyrimido[1,2-a]pyrimidin-4-one 1.2 g (3.93 mmol) of 2,8-dipyridin-4-yl-6,7,8,9-tetrahydro-4H-pyrimido[1,2-a]pyrimidin-4-one (compound No. 14.2) was separated by chiral preparative HPLC (CHIRALPAK AS) eluting with n-heptane/ethanol in the proportions 50/50 to give 0.572 g of pure product obtained in the form of free base. $t_R$: 12 min. Mp: 235-238° C. $[\alpha]_D^{20}$=−11.5° (c=0.394, DMSO).

22.2 (+)-9-(2-Oxo-2-phenyl-ethyl)-2,8-dipyridin-4-yl-6,7,8,9-tetrahydro-4H-pyrimido[1,2-a]pyrimidin-4-one hydrochloride (1:2)

The product was obtained by analogy with the method described in Example 14.3. Mp: 225-227° C. $[\alpha]_D^{20}$=+65.4° (c=0.521, DMSO).
$^1$H NMR (200 MHz; DMSO-d$^6$): δ (ppm) 8.9 (d, 2H); 8.7 (d, 2H); 8.0 (m, 6H); 7.8-7.5 (m, 3H); 6.7 (s, 1H); 5.75 (d, 1H); 5.3 (br s, 1H); 4.7 (d, 1H); 4.5 (m, 1 H); 3.1 (ddd, 1H); 2.5 (m, 2H).

A list of chemical structures and physical data for compounds of the aforementioned formula (I), illustrating the present invention, is given in Table 1. The compounds have been prepared according to the methods of the examples.

In Table 1, R1 is an unsubstituted pyrimidin-4-yl group or an unsubstituted pyridin-4-yl group, p represents 2, q represents 0, Ph represents a phenyl group, Me represents a methyl group; (+) and (−) indicates respectively a dextro and levo isomer; (S), (R) or (Rac.) indicates in the column "Y" or R4, the stereochemistry of the carbon atom: (rac.) means racemic mixture; (R) means absolute R configuration; (S) means absolute S configuration.

TABLE 1

(I)

| No | R2 | Y | X | R1 | R3 | R4 | R5 | q | p | n | Mp ° C. | salt |
|---|---|---|---|---|---|---|---|---|---|---|---|---|
| 1. | Ph | CH(OH)(S) | H,H | 4-pyridyl | H | Ph (Rac.) | H | 0 | 2 | 0 | 254-256 | (1:1) (hydro-chloride) |
| 2. | Ph | CO | H,H | 4-pyridyl | H | Ph (Rac.) | H | 0 | 2 | 0 | 134-137 | (1:1) (hydro-chloride) |
| 3. | 3-Br-Ph | CO | H,H | 4-pyridyl | H | Ph (Rac.) | H | 0 | 2 | 0 | 143-145 | (1:1) (hydro-chloride) |
| 4. | 4-Cl-Ph | CO | H,H | 4-pyridyl | H | Ph (Rac.) | H | 0 | 2 | 0 | 145-147 | (1:1) (hydro-chloride) |
| 5. | 4-F-Ph | CO | H,H | 4-pyridyl | H | Ph (Rac.) | H | 0 | 2 | 0 | 145-147 | (1:1) (hydro-chloride) |
| 6. | 3-F-Ph | CO | H,H | 4-pyridyl | H | Ph (Rac.) | H | 0 | 2 | 0 | 167-169 | (1:1) (hydro-chloride) |
| 7. | 4-MeO-Ph | CO | H,H | 4-pyridyl | H | Ph (Rac.) | H | 0 | 2 | 0 | 197-199 | (1:1) (hydro-chloride) |

TABLE 1-continued
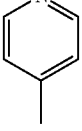
(I)
| No | R2 | Y | X | R1 | R3 | R4 | R5 | q | p | n | Mp °C. | salt |
|---|---|---|---|---|---|---|---|---|---|---|---|---|
| 8. | 4-N-Pyrro-lidine-Ph | CO | H,H | 4-pyridyl | H | Ph (Rac.) | H | 0 | 2 | 0 | 253-255 | Base |
| 9. | 4-Ph-Ph | CO | H,H | 4-pyridyl | H | Ph (Rac.) | H | 0 | 2 | 0 | 222-224 | Base |
| 10. | 4-Me-Ph | CO | H,H | 4-pyridyl | H | Ph (Rac.) | H | 0 | 2 | 0 | 209-211 | Base |
| 11. | 2-Naphthyl | CO | H,H | 4-pyridyl | H | Ph (Rac.) | H | 0 | 2 | 0 | 226-228 | Base |
| 12. | 3-MeO-Ph | CO | H,H | 4-pyridyl | H | Ph (Rac.) | H | 0 | 2 | 0 | 216-218 | Base |
| 13. | 2-MeO-Ph | CO | H,H | 4-pyridyl | H | Ph (Rac.) | H | 0 | 2 | 0 | 142-144 | Base |
| 14. | Ph | CO | H,H | 4-pyridyl | H | 4-pyridyl (Rac.) | H | 0 | 2 | 0 | 246-248 | Hydro-chloride (1:2) |

TABLE 1-continued
(I)
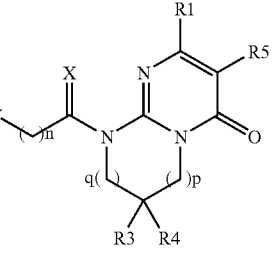
| No | R2 | Y | X | R1 | R3 | R4 | R5 | q | p | n | Mp ° C. | salt |
|---|---|---|---|---|---|---|---|---|---|---|---|---|
| 15. | 3-Br-Ph | CO | H,H | 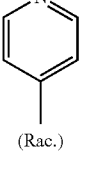 | H | 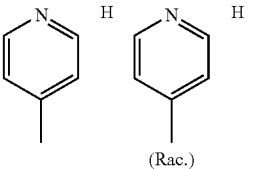<br>(Rac.) | H | 0 | 2 | 0 | 215-217 | Hydro-chloride (1:2) |
| 16. | Ph | (S)—CH(OH) | H,H | 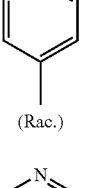 | H | 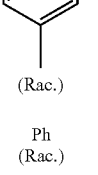<br>(Rac.) | H | 0 | 2 | 0 | 204-206 | Hydro-chloride (1:2) |
| 17. | 3-Br-Ph | CH(OH)<br>(Rac.) | H,H | 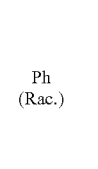 | H | 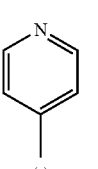<br>(Rac.) | H | 0 | 2 | 0 | 190-192 | Hydro-chloride (1:2) |
| 18. | 3-F-Ph | CO | H,H | 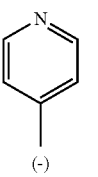 | H | 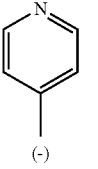<br>(Rac.) | H | 0 | 2 | 0 | 132-134 | Hydro-chloride (1:2) |
| 19. | 4-MeO-Ph | CH(OH)<br>(Rac.) | H,H | | H | Ph<br>(Rac.) | H | 0 | 2 | 0 | 150-152 | Base |
| 20. | 4-Me-Ph | CH(OH)<br>(Rac.) | H,H | | H | Ph<br>(Rac.) | H | 0 | 2 | 0 | 198-200 | Base |
| 21. | Ph | CO | H,H | | H | <br>(−) | H | 0 | 2 | 0 | 225-227 | Hydro-chloride (1:2) |

TABLE 1-continued
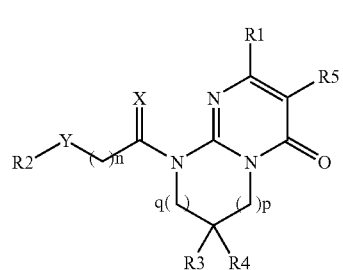
(I)
| No | R2 | Y | X | R1 | R3 | R4 | R5 | q | p | n | Mp °C. | salt |
|---|---|---|---|---|---|---|---|---|---|---|---|---|
| 22. | Ph | CO | H,H | 4-pyridyl | H | 4-pyridyl (+) | H | 0 | 2 | 0 | 225-227 | Hydro-chloride (1:2) |
| 23. | 3-Br-Ph | CH(OH) (Rac.) | H,H | 4-pyridyl | H | Ph (Rac.) | H | 0 | 2 | 0 | 170-172 | Base |
| 24. | 4-Cl-Ph | CH(OH) (Rac.) | H,H | 4-pyridyl | H | Ph (Rac.) | H | 0 | 2 | 0 | 220-222 | Base |
| 25. | 3-F-Ph | CH(OH) (Rac.) | H,H | 4-pyridyl | H | 4-pyridyl (Rac.) | H | 0 | 2 | 0 | 218-220 | Base |
| 26. | 4-F-Ph | CH(OH) (Rac.) | H,H | 4-pyridyl | H | Ph (Rac.) | H | 0 | 2 | 0 | 201-203 | Base |
| 27. | 4-Ph-Ph | CH(OH) (Rac.) | H,H | 4-pyridyl | H | Ph (Rac.) | H | 0 | 2 | 0 | 145-147 | Base |
| 28. | 2-Naphthyl | CH(OH) (Rac.) | H,H | 4-pyridyl | H | Ph (Rac.) | H | 0 | 2 | 0 | 190-192 | Base |

Test Example

Inhibitory Activity of the Medicament of the Present Invention Against GSK3β:

Two different protocols can be used.

In a first protocol: 7.5 μM of prephosphorylated GS1 peptide and 10 μM ATP (containing 300,000 cpm of 33P-ATP) were incubated in 25 mM Tris-HCl, pH 7.5, 0.6 mM DTT, 6 mM $MgCl_2$, 0.6 mM EGTA, 0.05 mg/ml BSA buffer for 1 hour at room temperature in the presence of GSK3beta (total reaction volume: 100 microliters).

In a second protocol: 4.1 μM of prephosphorylated GS1 peptide and 42 μM ATP (containing 260,000 cpm 33P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3beta. Inhibitors were solubilized in DMSO (final solvent concentration in the reaction medium, 1%).

The reaction was stopped with 100 microliters of a solution made of 25 g polyphosphoric acid (85% $P_2O_5$), 126 ml 85% $H_3PO_4$, $H_2O$ to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry. The phosphorylated GS-1 peptide had the following sequence:

NH2-YRRAAVPPSPSLSRHSSPHQS(P)EDEE-COOH.
SEQ ID NO: 1

The GSK3β inhibitory activity of the compounds of the present invention are expressed in $IC_{50}$, and as an illustration the range of $IC_{50}$'s of the compounds in Table 1 is between 1 nanomolar to 1 micromolar concentrations.

For example compound No. 15 of Table 1 shows an $IC_{50}$ of 0.007 μM.

Formulation Examples (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

INDUSTRIAL APPLICABILITY

The compounds of the present invention have GSK3β inhibitory activity and are useful as an active ingredient of a medicament for preventive and/or therapeutic treatment of diseases caused by abnormal activity of GSK3β and more particularly of neurodegenerative diseases.

---

What is claimed is:

1. A compound of formula (I) or a salt thereof

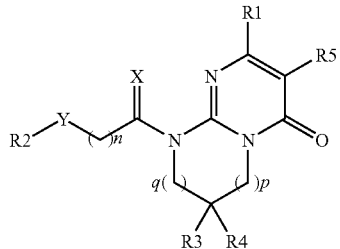

wherein:

X represents two hydrogen atoms, a sulfur atom, an oxygen atom or a $C_{1-2}$ alkyl group and a hydrogen atom;

Y represents a bond, a carbonyl group, a methylene group optionally substituted by one or two groups chosen from a $C_{1-6}$ alkyl group, a hydroxyl group, a $C_{1-4}$ alkoxy group, a $C_{1-2}$ perhalogenated alkyl group or an amino group;

R1 represents a 2, 3 or 4-pyridine ring or a 2, 4 or 5-pyrimidine ring, the rings being optionally substituted by a $C_{1-4}$ alkyl group, a $C_{1-4}$ alkoxy group or a halogen atom;

R2 represents a phenyl group or a naphthalene ring; the phenyl group or the naphthalene ring being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a phenyl group, a pyrrolidine ring, a piperidine ring or an azepine ring;

R3 represents a hydrogen atom or a $C_{1-6}$ alkyl group;

R4 represents a phenyl group, a naphthalene ring or a pyridinyl group, the groups and the ring being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group or a $C_{2-10}$ dialkylamino group;

R5 represents a hydrogen atom, a $C_{1-6}$ alkyl group or a halogen atom;

n represents 0 to 3; and p+q=0-3.

2. The compound of formula (I) according to claim 1, wherein R4 represents a phenyl group or a pyridinyl group.

3. The compound of formula (I) according to claim 2, wherein

R1 represents an unsubstituted 4-pyridinyl ring or a 4-pyrimidinyl ring;

R2 represents a phenyl group or a naphthalene ring, the phenyl group and the naphthalene ring being optionally substituted by 1 to 4 substituents selected from a $C_{1-3}$ alkyl group, a halogen atom, a hydroxyl group, a $C_{1-2}$ alkoxy group, a phenyl group, a pyrrolidine ring, a piperidine ring or an azepine ring;

R3 represents a hydrogen atom;

R5 represents a hydrogen atom;

X represents two hydrogen atoms;

Y represents a carbonyl group or a methylene group optionally substituted by a hydroxyl group; and n, p and q represent 0, 2 and 0, respectively.

4. The compound of formula (I) according to claim 1, which is selected from the group consisting of:

1'-[(2S)-2-hydroxy-2-phenyl-ethyl]-8-phenyl-2-(4-pyridinyl)-6,7,8,9-tetrahydro-4H-pyrimido[1,2-a]pyrimidin-4-one;

9-(2-oxo-2-phenyl-ethyl)-8-phenyl-2-(4-pyridinyl)-6,7,8,9-tetrahydro-4H-pyrimido[1,2-a]pyrimidin-4-one;

9-[2-(3-bromo-phenyl)-2-oxo-ethyl]-8-phenyl-2-(4-pyridinyl)-6,7,8,9-tetrahydro-4H-pyrimido[1,2-a]pyrimidin-4-one;

9-[2-(4-chloro-phenyl)-2-oxo-ethyl]-8-phenyl-2-(4-pyridinyl)-6,7,8,9-tetrahydro-4H-pyrimido[1,2-a]pyrimidin-4-one;

9-[2-(4-fluoro-phenyl)-2-oxo-ethyl]-8-phenyl-2-(4-pyridinyl)-6,7,8,9-tetrahydro-4H-pyrimido[1,2-a]pyrimidin-4-one;

9-[2-(3-fluoro-phenyl)-2-oxo-ethyl]-8-phenyl-2-(4-pyridinyl)-6,7,8,9-tetrahydro-4H-pyrimido[1,2-a]pyrimidin-4-one;

9-[2-(4-methoxy-phenyl)-2-oxo-ethyl]-8-phenyl-2-(4-pyridinyl)-6,7,8,9-tetrahydro-4H-pyrimido[1,2-a]pyrimidin-4-one;

9-[2-(oxo-2-(4-pyrrolidin-1-yl-phenyl)-ethyl]-8-phenyl-2-(4-pyridinyl)-6,7,8,9-tetrahydro-4H-pyrimido[1,2-a]pyrimidin-4-one;

9-(2-biphenyl-4-yl-2-oxo-ethyl)-8-phenyl-2-(4-pyridinyl)-6,7,8,9-tetrahydro-4H-pyrimido[1,2-a]pyrimidin-4-one;

9-(2-oxo-2-p-tolyl-ethyl)-8-phenyl-2-(4-pyridinyl)-6,7,8,9-tetrahydro-4H-pyrimido[1,2-a]pyrimidin-4-one;

9-(2-naphthalen-2-yl-2-oxo-ethyl)-8-phenyl-2-(4-pyridinyl)-6,7,8,9-tetrahydro-4H-pyrimido[1,2-a]pyrimidin-4-one;

9-[2-(3-methoxy-phenyl)-2-oxo-ethyl]-8-phenyl-2-(4-pyridinyl)-6,7,8,9-tetrahydro-4H-pyrimido[1,2-a]pyrimidin-4-one;

9-[2-(2-methoxy-phenyl)-2-oxo-ethyl]-8-phenyl-2-(4-pyridinyl)-6,7,8,9-tetrahydro-4H-pyrimido[1,2-a]pyrimidin-4-one;

9-[(2S)-2-oxo-2-phenyl-ethyl]-2,8-dipyridin-4-yl-6,7,8,9-tetrahydro-4H-pyrimido[1,2-a]pyrimidin-4-one;

9-[2-(3-bromo-phenyl)-2-oxo-ethyl]-2,8-dipyridin-4-yl-6,7,8,9-tetrahydro-pyrimido[1,2-a]pyrimidin-4-one;

9-(2-hydroxy-2-phenyl-ethyl)-2,8-dipyridin-4-yl-6,7,8,9-tetrahydro-pyrimido[1,2-a]pyrimidin-4-one;

9-[2-(3-bromo-phenyl)-2-hydroxy-ethyl]-2,8-dipyridin-4-yl-6,7,8,9-tetrahydro-pyrimido[1,2-a]pyrimidin-4-one;

9-[2-(3-fluoro-phenyl)-2-oxo-ethyl]-2,8-dipyridin-4-yl-6,7,8,9-tetrahydro-pyrimido[1,2-a]pyrimidin-4-one;

9-[2-hydroxy-2-(4-methoxy-phenyl)-ethyl]-8-phenyl-2-pyridin-4-yl-6,7,8,9-tetrahydro-pyrimido[1,2-a]pyrimidin-4-one;

9-(2-hydroxy-2-p-tolyl-ethyl)-8-phenyl-2-pyridin-4-yl-6,7,8,9-tetrahydro-pyrimido[1,2-a]pyrimidin-4-one;

(−)-9-(2-oxo-2-phenyl-ethyl)-2,8-dipyridin-4-yl-6,7,8,9-tetrahydro-4H-pyrimido[1,2-a]pyrimidin-4-one;

(+)-9-(2-oxo-2-phenyl-ethyl)-2,8-dipyridin-4-yl-6,7,8,9-tetrahydro-4H-pyrimido[1,2-a]pyrimidin-4-one;

9-[2-hydroxy-2-(3-bromo-phenyl)-ethyl]-8-phenyl-2-pyridin-4-yl-6,7,8,9-tetrahydro-pyrimido[1,2-a]pyrimidin-4-one;

9-[2-hydroxy-2-(4-chloro-phenyl)-ethyl]-8-phenyl-2-pyridin-4-yl-6,7,8,9-tetrahydro-pyrimido[1,2-a]pyrimidin-4-one;

9-[2-(3-fluoro-phenyl)-2-hydroxy-ethyl]-2,8-dipyridin-4-yl-6,7,8,9-tetrahydro-pyrimido[1,2-a]pyrimidin-4-one;

9-[2-hydroxy-2-(4-fluoro-phenyl)-ethyl]-8-phenyl-2-pyridin-4-yl-6,7,8,9-tetrahydro-pyrimido[1,2-a]pyrimidin-4-one;

9-[2-hydroxy-2-(4-phenyl-phenyl)-ethyl]-8-phenyl-2-pyridin-4-yl-6,7,8,9-tetrahydro-pyrimido[1,2-a]pyrimidin-4-one; and 9-[2-hydroxy-2-naphthalen-2-yl-ethyl]-8-phenyl-2-pyridin-4-yl-6,7,8,9-tetrahydro-pyrimido[1,2-a]pyrimidin-4-one;

or a salt thereof.

5. A compound of formula (III)

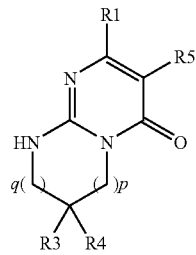

(III)

wherein p+q=0-3;

R1 represents a 2, 3 or 4-pyridine ring or a 2, 4 or 5-pyrimidine ring, the rings being optionally substituted by a $C_{1-4}$ alkyl group, a $C_{1-4}$ alkoxy group or a halogen atom;

R3 represents a hydrogen atom or a $C_{1-6}$ alkyl group;

R4 represents a phenyl group, a naphthalene ring or a pyridinyl group, the groups and the ring being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group or a $C_{2-10}$ dialkylamino group; and R5 represents a hydrogen atom, a $C_{1-6}$ alkyl group or a halogen atom.

6. A pharmaceutical composition comprising a compound of formula (I) or a pharmaceutically acceptable salt thereof, or a solvate thereof, according to claim 1 in combination with one or more pharmaceutically acceptable diluent, excipient or a carrier.

7. The pharmaceutical composition according to claim 6, wherein the compound of formula (I) is selected from the group consisting of:

1'-[(2S)-2-hydroxy-2-phenyl-ethyl]-8-phenyl-2-(4-pyridinyl)-6,7,8,9-tetrahydro-4H-pyrimido[1,2-a]pyrimidin-4-one;

9-(2-oxo-2-phenyl-ethyl)-8-phenyl-2-(4-pyridinyl)-6,7,8,9-tetrahydro-4H-pyrimido[1,2-a]pyrimidin-4-one;

9-[2-(3-bromo-phenyl)-2-oxo-ethyl]-8-phenyl-2-(4-pyridinyl)-6,7,8,9-tetrahydro-4H-pyrimido[1,2-a]pyrimidin-4-one;

9-[2-(4-chloro-phenyl)-2-oxo-ethyl]-8-phenyl-2-(4-pyridinyl)-6,7,8,9-tetrahydro-4H-pyrimido[1,2-a]pyrimidin-4-one;

9-[2-(4-fluoro-phenyl)-2-oxo-ethyl]-8-phenyl-2-(4-pyridinyl)-6,7,8,9-tetrahydro-4H-pyrimido[1,2-a]pyrimidin-4-one;

9-[2-(3-fluoro-phenyl)-2-oxo-ethyl]-8-phenyl-2-(4-pyridinyl)-6,7,8,9-tetrahydro-4H-pyrimido[1,2-a]pyrimidin-4-one;

9-[2-(4-methoxy-phenyl)-2-oxo-ethyl]-8-phenyl-2-(4-pyridinyl)-6,7,8,9-tetrahydro-4H-pyrimido[1,2-a]pyrimidin-4-one;

9-[2-(oxo-2-(4-pyrrolidin-1-yl-phenyl)-ethyl]-8-phenyl-2-(4-pyridinyl)-6,7,8,9-tetrahydro-4H-pyrimido[1,2-a]pyrimidin-4-one;

9-(2-biphenyl-4-yl-2-oxo-ethyl)-8-phenyl-2-(4-pyridinyl)-6,7,8,9-tetrahydro-4H-pyrimido[1,2-a]pyrimidin-4-one;

9-(2-oxo-2-p-tolyl-ethyl)-8-phenyl-2-(4-pyridinyl)-6,7,8,9-tetrahydro-4H-pyrimido[1,2-a]pyrimidin-4-one;

9-(2-naphthalen-2-yl-2-oxo-ethyl)-8-phenyl-2-(4-pyridinyl)-6,7,8,9-tetrahydro-4H-pyrimido[1,2-a]pyrimidin-4-one;

9-[2-(3-methoxy-phenyl)-2-oxo-ethyl]-8-phenyl-2-(4-pyridinyl)-6,7,8,9-tetrahydro-4H-pyrimido[1,2-a]pyrimidin-4-one;

9-[2-(2-methoxy-phenyl)-2-oxo-ethyl]-8-phenyl-2-(4-pyridinyl)-6,7,8,9-tetrahydro-4H-pyrimido[1,2-a]pyrimidin-4-one;

9-[(2S)-2-oxo-2-phenyl-ethyl]-2,8-dipyridin-4-yl-6,7,8,9-tetrahydro-4H-pyrimido[1,2-a]pyrimidin-4-one;

9-[2-(3-bromo-phenyl)-2-oxo-ethyl]-2,8-dipyridin-4-yl-6,7,8,9-tetrahydro-pyrimido[1,2-a]pyrimidin-4-one;

9-(2-hydroxy-2-phenyl-ethyl)-2,8-dipyridin-4-yl-6,7,8,9-tetrahydro-pyrimido[1,2-a]pyrimidin-4-one;

9-[2-(3-bromo-phenyl)-2-hydroxy-ethyl]-2,8-dipyridin-4-yl-6,7,8,9-tetrahydro-pyrimido[1,2-a]pyrimidin-4-one;

9-[2-(3-fluoro-phenyl)-2-oxo-ethyl]-2,8-dipyridin-4-yl-6,7,8,9-tetrahydro-pyrimido[1,2-a]pyrimidin-4-one;

9-[2-hydroxy-2-(4-methoxy-phenyl)-ethyl]-8-phenyl-2-pyridin-4-yl-6,7,8,9-tetrahydro-pyrimido[1,2-a]pyrimidin-4-one;

9-(2-hydroxy-2-p-tolyl-ethyl)-8-phenyl-2-pyridin-4-yl-6,7,8,9-tetrahydro-pyrimido[1,2-a]pyrimidin-4-one;

(−)-9-(2-oxo-2-phenyl-ethyl)-2,8-dipyridin-4-yl-6,7,8,9-tetrahydro-4H-pyrimido[1,2-a]pyrimidin-4-one;

(+)-9-(2-oxo-2-phenyl-ethyl)-2,8-dipyridin-4-yl-6,7,8,9-tetrahydro-4H-pyrimido[1,2-a]pyrimidin-4-one;

9-[2-hydroxy-2-(3-bromo-phenyl)-ethyl]-8-phenyl-2-pyridin-4-yl-6,7,8,9-tetrahydro-pyrimido[1,2-a]pyrimidin-4-one;

9-[2-hydroxy-2-(4-chloro-phenyl)-ethyl]-8-phenyl-2-pyridin-4-yl-6,7,8,9-tetrahydro-pyrimido[1,2-a]pyrimidin-4-one;

9-[2-(3-fluoro-phenyl)-2-hydroxy-ethyl]-2,8-dipyridin-4-yl-6,7,8,9-tetrahydro-pyrimido[1,2-a]pyrimidin-4-one;

9-[2-hydroxy-2-(4-fluoro-phenyl)-ethyl]-8-phenyl-2-pyridin-4-yl-6,7,8,9-tetrahydro-pyrimido[1,2-a]pyrimidin-4-one;

9-[2-hydroxy-2-(4-phenyl-phenyl)-ethyl]-8-phenyl-2-pyridin-4-yl-6,7,8,9-tetrahydro-pyrimido[1,2-a]pyrimidin-4-one;

9-[2-hydroxy-2-naphthalen-2-yl-ethyl]-8-phenyl-2-pyridin-4-yl-6,7,8,9-tetrahydro-pyrimido[1,2-a]pyrimidin-4-one;

or a salt thereof.

8. A method of treating a disease in a patient, said disease selected from the group consisting of Alzheimer's disease, Parkinson's disease, taupathies, noninsulin dependent diabetes, obesity, manic depressive illness and schizophrenia, comprising administering to said patient a therapeutically effective amount of a compound of formula (I) or a pharmaceutically acceptable salt thereof:

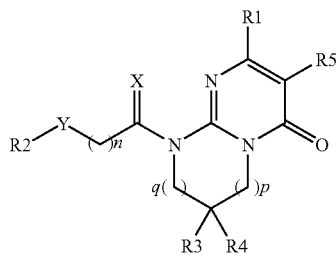

wherein:
X represents two hydrogen atoms, a sulfur atom, an oxygen atom or a $C_{1-2}$ alkyl group and a hydrogen atom;
Y represents a bond, a carbonyl group, a methylene group optionally substituted by one or two groups chosen from a $C_{1-6}$ alkyl group, a hydroxyl group, a $C_{1-4}$ alkoxy group, a $C_{1-2}$ perhalogenated alkyl group or an amino group;
R1 represents a 2, 3 or 4-pyridine ring or a 2, 4 or 5-pyrimidine ring, the rings being optionally substituted by a $C_{1-4}$ alkyl group, a $C_{1-4}$ alkoxy group or a halogen atom;
R2 represents a phenyl group or a naphthalene ring; the phenyl group or the naphthalene ring being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a phenyl group, a pyrrolidine ring, a piperidine ring or an azepine ring;
R3 represents a hydrogen atom or a $C_{1-6}$ alkyl group;
R4 represents a phenyl group, a naphthalene ring or a pyridinyl group, the groups and the ring being optionally substituted by 1 to 4 substituents selected from a $C_{1-6}$ alkyl group, a methylenedioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group or a $C_{2-10}$ dialkylamino group;
R5 represents a hydrogen atom, a $C_{1-6}$ alkyl group or a halogen atom;
n represents 0 to 3; and p+q=0-3.

9. The method according to claim 8, wherein R4 represents a phenyl group or a pyridinyl group.

10. The method according to claim 9, wherein
R1 represents an unsubstituted 4-pyridinyl ring or a 4-pyrimidinyl ring;
R2 represents a phenyl group or a naphthalene ring, the phenyl group and the naphthalene ring being optionally substituted by 1 to 4 substituents selected from a $C_{1-3}$ alkyl group, a halogen atom, a hydroxyl group, a $C_{1-2}$ alkoxy group, a phenyl group, a pyrrolidine ring, a piperidine ring or an azepine ring;
R3 represents a hydrogen atom;
R5 represents a hydrogen atom;
X represents two hydrogen atoms;
Y represents a carbonyl group or a methylene group optionally substituted by a hydroxyl group; and
n, p and q represent 0, 2 and 0, respectively.

11. The method according to claim 8, wherein the compound of formula (I) is selected from the group consisting of:
1'-[(2S)-2-hydroxy-2-phenyl-ethyl]-8-phenyl-2-(4-pyridinyl)-6,7,8,9-tetrahydro-4H-pyrimido[1,2-a]pyrimidin-4-one;
9-(2-oxo-2-phenyl-ethyl)-8-phenyl-2-(4-pyridinyl)-6,7,8,9-tetrahydro-4H-pyrimido[1,2-a]pyrimidin-4-one;
9-[2-(3-bromo-phenyl)-2-oxo-ethyl]-8-phenyl-2-(4-pyridinyl)-6,7,8,9-tetrahydro-4H-pyrimido[1,2-a]pyrimidin-4-one;
9-[2-(4-chloro-phenyl)-2-oxo-ethyl]-8-phenyl-2-(4-pyridinyl)-6,7,8,9-tetrahydro-4H-pyrimido[1,2-a]pyrimidin-4-one;
9-[2-(4-fluoro-phenyl)-2-oxo-ethyl]-8-phenyl-2-(4-pyridinyl)-6,7,8,9-tetrahydro-4H-pyrimido[1,2-a]pyrimidin-4-one;
9-[2-(3-fluoro-phenyl)-2-oxo-ethyl]-8-phenyl-2-(4-pyridinyl)-6,7,8,9-tetrahydro-4H-pyrimido[1,2-a]pyrimidin-4-one;
9-[2-(4-methoxy-phenyl)-2-oxo-ethyl]-8-phenyl-2-(4-pyridinyl)-6,7,8,9-tetrahydro-4H-pyrimido[1,2-a]pyrimidin-4-one;
9-[2-(oxo-2-(4-pyrrolidin-1-yl-phenyl)-ethyl]-8-phenyl-2-(4-pyridinyl)-6,7,8,9-tetrahydro-4H-pyrimido[1,2-a]pyrimidin-4-one;
9-(2-biphenyl-4-yl-2-oxo-ethyl)-8-phenyl-2-(4-pyridinyl)-6,7,8,9-tetrahydro-4H-pyrimido[1,2-a]pyrimidin-4-one;
9-(2-oxo-2-p-tolyl-ethyl)-8-phenyl-2-(4-pyridinyl)-6,7,8,9-tetrahydro-4H-pyrimido[1,2-a]pyrimidin-4-one;
9-(2-naphthalen-2-yl-2-oxo-ethyl)-8-phenyl-2-(4-pyridinyl)-6,7,8,9-tetrahydro-4H-pyrimido[1,2-a]pyrimidin-4-one;
9-[2-(3-methoxy-phenyl)-2-oxo-ethyl]-8-phenyl-2-(4-pyridinyl)-6,7,8,9-tetrahydro-4H-pyrimido[1,2-a]pyrimidin-4-one;
9-[2-(2-methoxy-phenyl)-2-oxo-ethyl]-8-phenyl-2-(4-pyridinyl)-6,7,8,9-tetrahydro-4H-pyrimido[1,2-a]pyrimidin-4-one;
9-[(2S)-2-oxo-2-phenyl-ethyl]-2,8-dipyridin-4-yl-6,7,8,9-tetrahydro-4H-pyrimido[1,2-a]pyrimidin-4-one;
9-[2-(3-bromo-phenyl)-2-oxo-ethyl]-2,8-dipyridin-4-yl-6,7,8,9-tetrahydro-pyrimido[1,2-a]pyrimidin-4-one;
9-(2-hydroxy-2-phenyl-ethyl)-2,8-dipyridin-4-yl-6,7,8,9-tetrahydro-pyrimido[1,2-a]pyrimidin-4-one;
9-[2-(3-bromo-phenyl)-2-hydroxy-ethyl]-2,8-dipyridin-4-yl-6,7,8,9-tetrahydro-pyrimido[1,2-a]pyrimidin-4-one;
9-[2-(3-fluoro-phenyl)-2-oxo-ethyl]-2,8dipyridin-4-yl-6,7,8,9-tetrahydro-pyrimido[1,2-a]pyrimidin-4-one;
9-[2-hydroxy-2-(4-methoxy-phenyl)-ethyl]-8-phenyl-2-pyridin-4-yl-6,7,8,9-tetrahydro-pyrimido[1,2-a]pyrimidin-4-one;
9-(2-hydroxy-2-p-tolyl-ethyl)-8-phenyl-2-pyridin-4-yl-6,7,8,9-tetrahydro-pyrimido[1,2-a]pyrimidin-4-one;
(−)-9-(2-oxo-2-phenyl-ethyl)-2,8-dipyridin-4-yl-6,7,8,9-tetrahydro-4H-pyrimido[1,2-a]pyrimidin-4-one;
(+)-9-(2-oxo-2-phenyl-ethyl)-2,8-dipyridin-4-yl-6,7,8,9-tetrahydro-4H-pyrimido[1,2-a]pyrimidin-4-one;
9-[2-hydroxy-2-(3-bromo-phenyl)-ethyl]-8-phenyl-2-pyridin-4-yl-6,7,8,9-tetrahydro-pyrimido[1,2-a]pyrimidin-4-one;

9-[2-hydroxy-2-(4-chloro-phenyl)-ethyl]-8-phenyl-2-pyridin-4-yl-6,7,8,9-tetrahydro-pyrimido[1,2-a]pyrimidin-4-one;

9-[2-(3-fluoro-phenyl)-2-hydroxy-ethyl]-2,8-dipyridin-4-yl-6,7,8,9-tetrahydro-pyrimido[1,2-a]pyrimidin-4-one;

9-[2-hydroxy-2-(4-fluoro-phenyl)-ethyl]-8-phenyl-2-pyridin-4-yl-6,7,8,9-tetrahydro-pyrimido[1,2-a]pyrimidin-4-one;

9-[2-hydroxy-2-(4-phenyl-phenyl)-ethyl]-8-phenyl-2-pyridin-4-yl-6,7,8,9-tetrahydro-pyrimido[1,2-a]pyrimidin-4-one; and 9-[2-hydroxy-2-naphthalen-2-yl-ethyl]-8-phenyl-2-pyridin-4-yl-6,7,8,9-tetrahydro-pyrimido[1,2-a]pyrimidin-4-one;

or a salt thereof.

12. The method according to claim 8, wherein the disease is selected from the group consisting of Alheimer's disease, Parkinson's disease and taupathies.

13. The method according to claim 12, wherein the disease is Alzheimer's disease.

14. The method according to claim 12, wherein the disease is Parkinson's disease.

15. The method according to claim 12, wherein the disease is taupathies.

16. The method according to claim 8, wherein the disease is selected from the group consisting of non-insulin dependent diabetes; obesity; manic depressive illness; and schizophrenia.

17. The method according to claim 16, wherein the disease is non-insulin dependent diabetes.

* * * * *

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial
<220> FEATURE:
<223> OTHER INFORMATION: GS1 peptide
<220> FEATURE:
<221> NAME/KEY: MISC_FEATURE
<222> LOCATION: (21)..(21)
<223> OTHER INFORMATION: Phosphorylated

<400> SEQUENCE: 1

Tyr Arg Arg Ala Ala Val Pro Pro Ser Pro Ser Leu Ser Arg His Ser
1               5                   10                  15

Ser Pro His Gln Ser Glu Asp Gln Gln
            20                  25
```